US00PP26798P3

(12) United States Plant Patent
Schiappacasse Macchiavello

(10) Patent No.: US PP26,798 P3
(45) Date of Patent: Jun. 7, 2016

(54) AVOCADO TREE NAMED 'FLAVIA'

(50) Latin Name: ***Persea americana* Mill.**
Varietal Denomination: Flavia

(71) Applicant: AGROFRUTICOLA SAN BERNARDO DE MALLARAUCO LIMITADA, Santiago (CL)

(72) Inventor: Alfredo Schiappacasse Macchiavello, Santiago (CL)

( * ) Notice: Subject to any disclaimer, the term of this patent is extended or adjusted under 35 U.S.C. 154(b) by 273 days.

(21) Appl. No.: 13/815,426

(22) Filed: Feb. 28, 2013

(65) Prior Publication Data

US 2014/0245501 P1 Aug. 28, 2014

(51) Int. Cl.
*A01H 5/08* (2006.01)

(52) U.S. Cl.
USPC ..... Plt./200
CPC ..... *A01H 5/0818* (2013.01)

(58) Field of Classification Search
USPC ..... Plt./200
CPC ..... A01H 5/0818; A01H 5/08
See application file for complete search history.

(56) References Cited

U.S. PATENT DOCUMENTS

| | | | | |
|---|---|---|---|---|
| PP139 | P | 8/1935 | Hass | |
| PP5,309 | P | 10/1984 | Whitsell | |
| PP17,947 | P3 * | 8/2007 | Darvas | Plt./200 |
| PP23,885 | P3 * | 9/2013 | Pflum | Plt./200 |
| PP24,279 | P3 * | 3/2014 | Menge et al. | Plt./200 |

OTHER PUBLICATIONS

Francisco Gardiazabal I. et al.; Evaluation of Two New Hass Type Varieties Found in Chile; 11 pages, 2007.

Michael T. Clegg et al.; Assessing the Genetic Determination of Valuable Avocado Traits . . . ; 2007 Production Research Report, California Avocado Commission; 5 pages.

* cited by examiner

*Primary Examiner* — Kent L Bell
(74) *Attorney, Agent, or Firm* — Kelly & Kelley, LLP

(57) ABSTRACT

A new variety, 'Flavia', was discovered in an avocado orchard in Chile. The 'Flavia' avocado is notable for its larger fruit and seed size as compared to 'Hass'. 'Flavia' also has earlier fruit maturity for harvesting than 'Hass'.

7 Drawing Sheets

Latin name of the genus and species: *Persea americana* Mill.

Varietal denomination: 'Flavia'.

BACKGROUND OF THE INVENTION

Currently, the main avocado variety in the world is 'Hass' (U.S. Plant Pat. No. 139, the contents of which are incorporated herein by reference). The main markets have year-round supply of 'Hass' avocados and end consumers are very used to buying 'Hass'. Final consumers are used to buying and eating 'Hass' avocados. Many other avocado varieties have been created and patented in the last few decades, but none of them has been able to obtain important interest from growers as there is a lack of interest in the market which still prefers 'Hass'.

In the past few years, avocado fruit size has become one of the challenges that avocado growers are facing. Net returns can be doubled when growers move from small fruit to big fruit (+200 grams). There are varieties, such as 'Esther', U.S. Plant Pat. No. 5,309) that solved the fruit size problem by providing a larger fruit. However, the skin of the fruit is green and the market has no major interest for green skin avocado varieties.

SUMMARY OF THE INVENTION

'Flavia' is a new and distinct variety of avocado tree *Persea americana* Mill. The variety was first discovered in 1998 by Alfredo Schiappacasse Macchiavello, who noted a tree that produced bigger fruit in his compact 'Hass' cultivated avocado orchard in the Mallarauco Valley in Chile.

The 'Flavia' discovered tree is a spontaneously mutated bud (a whole tree mutation) from 'Hass'. Budwood from the originally discovered tree was grafted into new trees and planted in 2001 as a non-propagation trial in Quillota, Chile, and has since been observed to remain true to type over successive asexually propagated generations.

The tree was discovered, after observing through several years, to have fruit size that was consistently larger than the other 'Hass' trees from the orchard. After several evaluations, it has been determined that the tree consistently produces larger fruit than 'Hass'. Moreover, 'Flavia' reaches minimum dry matter level (23% DM), and thus can be harvested, four to five weeks earlier than regular 'Hass'. Also, the stem is wider than in 'Hass', which is a characteristic in more than 80% of the 'Flavia' fruits.

BRIEF DESCRIPTION OF THE PHOTOGRAPHS

The accompanying photographs show specimens of the tree and plant parts of the new 'Flavia' variety.

DETAILED BOTANICAL DESCRIPTION OF THE VARIETY

The following detailed botanical description is based on observations and evaluations conducted between 2003 and 2006 of a trial planted in 2001 in Quillota, Chile. 'Flavia' at times is referred to by the code names GAMA 4022 or Andes 3. The four-year study evaluated and compared the 'Flavia' trees to similar trees grafted with 'Hass'. Budwood from the mother 'Flavia' tree, shown in FIGS. 1 and 2, was grafted into new trees which were planted as part of the non-propagation trial.

Aside from the fact that the 'Flavia' produces larger fruit than the regular 'Hass', and reaches dry minimum matter level four to five weeks earlier than regular 'Hass', it is otherwise nearly identical in color and appearance as to regular 'Hass' trees.

Figure 1:
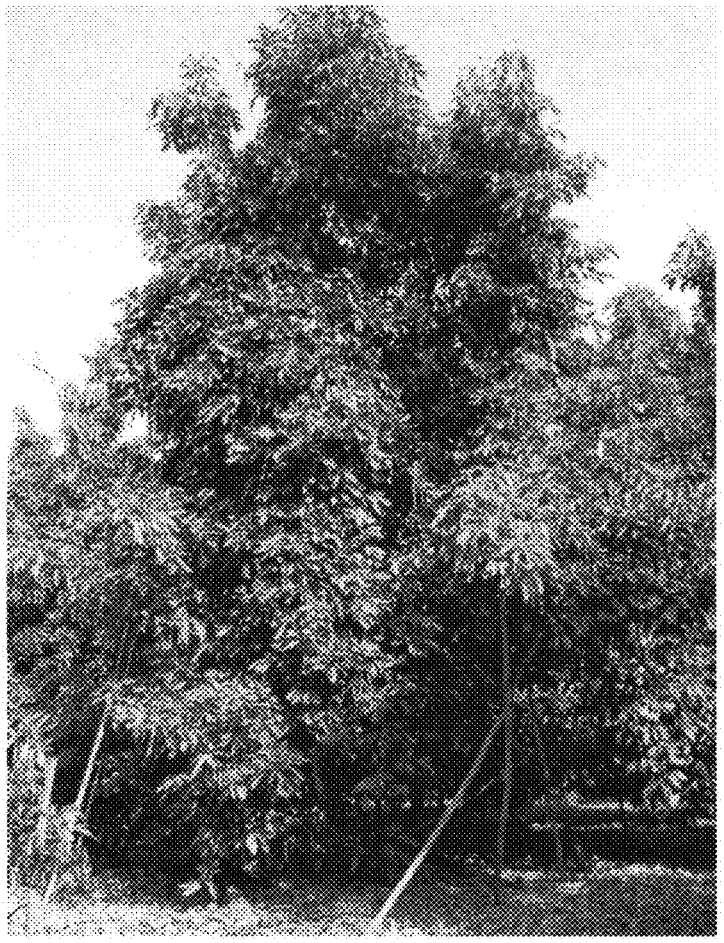
FIG. 1 is a photograph of the originally discovered 'Flavia' mother tree.
Figure 2:
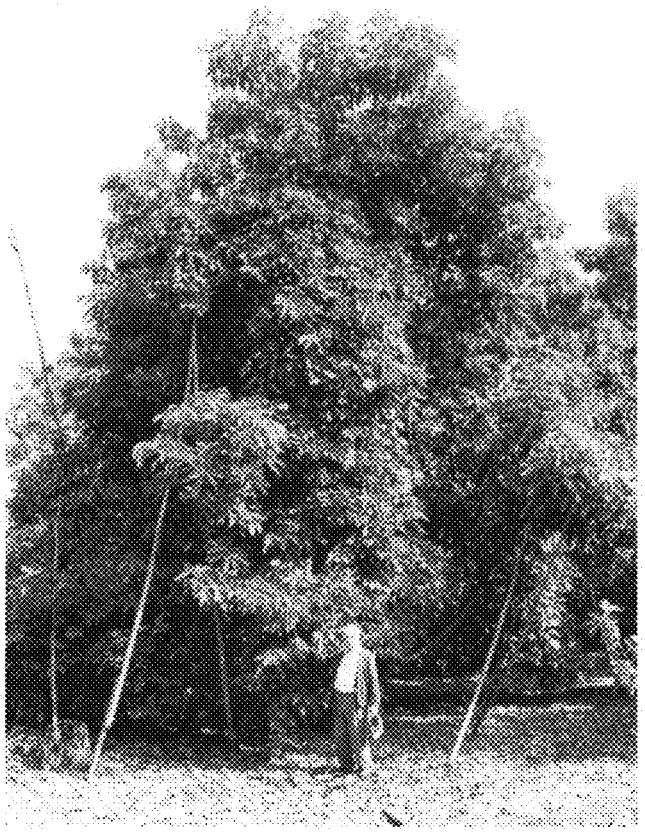
FIG. 2 is a photograph of the originally discovered 'Flavia' mother tree with a man for size reference.

More particularly, the tree presents a vigorous upright growth, as illustrated in FIGS. 1 and 2. The young shoots are reddish in color. The young shoot lenticels are purple in color. The anise aroma of the leaf blade is absent or very weak, similar to 'Hass'. The inflorescence flowering type is similar to 'Hass' Type A.

The main botanical characteristics of the tree, including the leafs and flowers thereof are as follows:

Tree growth habit: Spreading.

Leaf blade anise aroma: Absent or weak.

Flowering type: A.

Seed (shape in longitudinal section): Ovate.

Tree size compared to 'Hass' (5 year old trees) planted at 6×2 m:

1. *'Flavia'*.—Total Height: 3.56 meters (m). Length in Row: 2.62 m. Length Between rows: 3.42 m.
2. *'Hass'*.—Total Height: 4.15 m. Length Between Row: 2.78 m. Length Between rows: 4.06 m.

Vegetative structures colors:

*Pedicel*.—Pantone 2290C.

*Spring vegetative flush*.—Pantone 2278C.

1 *year old twig*.—Pantone 370C.

*Twigs older than* 1 *year*.—Pantone 7741C.

Leaf description:

1. *Color*.—Upper Side color: Pantone 7735CP. Lower side color: Pantone 2263CP.
2. *Shape*.—Limb: Elliptic. Apex: Acuminate. Leaf torsion in all length: Absent. Torsion of the apex: Absent. Leaf Border undulation: Medium.

Leaf size: Mature spring flush.

| | 'Hass' | 'Flavia' |
|---|---|---|
| Length (cm) | 15.28 | 15.46 |
| Width (cm) | 6.45 | 6.47 |
| Pedicel Length (cm) | 4.85 | 4.98 |
| Relation Length/Width | 2.38 | 2.41 |

Flower description:

*Flower type*.—A.

*Developing inflorescence*.—Pantone 7486C-Pantone 7485C.

*Expanded inflorescence*.—Pantone 393C.

TABLE 1

Trunk Perimeter of 'Hass' and 'Flavia'

| Year | 'Hass' | 'Flavia' |
|---|---|---|
| 2003 | 23.9 s | What is claimed is: 0.1 s |
| What is claimed is: 004 | What is claimed is: 4.3 s | What is claimed is: 0.4 s |
| What is claimed is: 005 | What is claimed is: 5.1 | What is claimed is: 2.7 |
| What is claimed is: 006 | What is claimed is: 1.4 s | What is claimed is: 7.6 s |

In each row "s" indicates statistical difference (T-Student. $P<0.05$).

Figure 3:
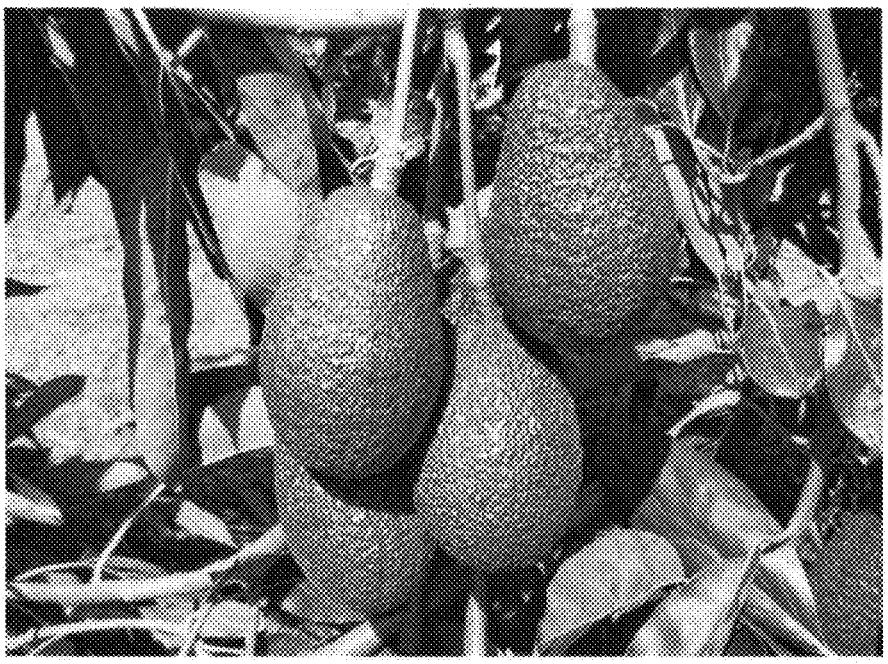
FIG. 3 is a photograph depicting fruit and leaves of 'Flavia'.
Figure 4:
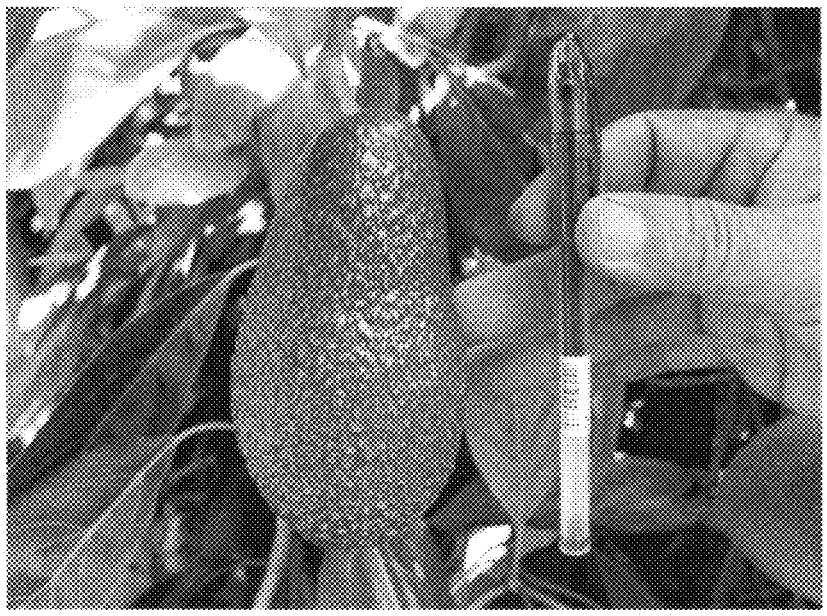
FIG. 4 is a photograph depicting fruit and leaves next to a hand holding a pen for size reference.
Figure 5:
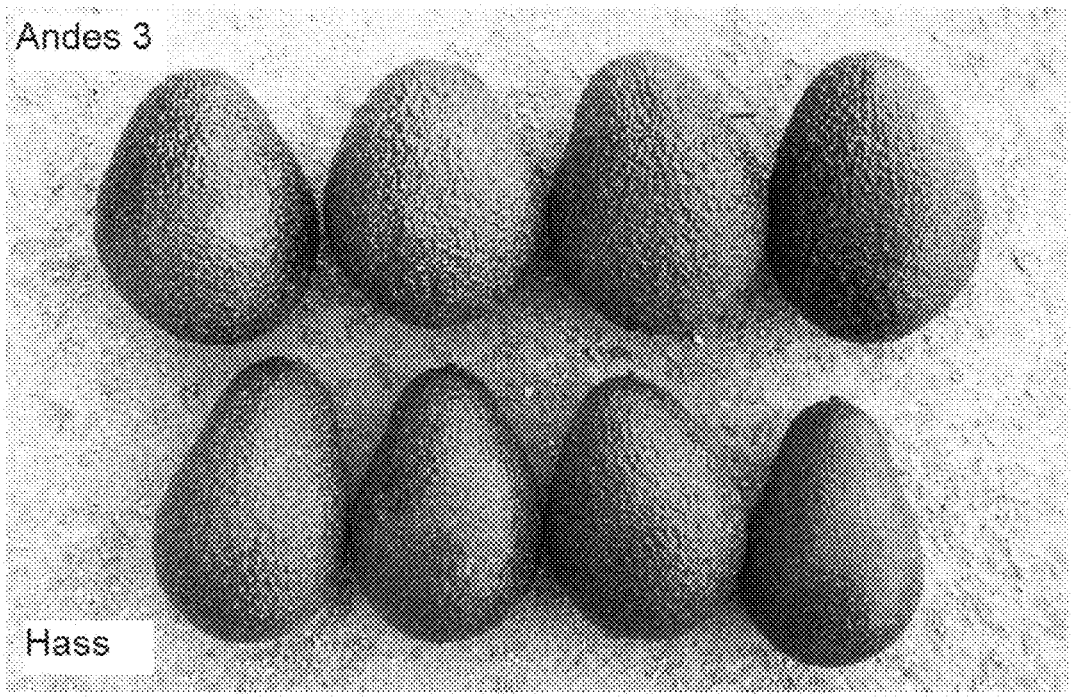
FIG. 5 is a photograph of four 'Flavia' fruit above four typical 'Hass' fruit, illustrating the enlarged nature of the 'Flavia' fruit.

With respect to the fruit, the surface of the mature fruit is rough, similar to 'Hass', as shown in FIGS. 3-5. The thickness of the pedicel compared to the peduncle, at the junction, is thicker. The pedicel length is medium. The pedicel shape is cylindrical. There is no "nail head" pedicel. The thickness of the ripe fruit skin is moderately thick, similar to 'Hass'. Also similar to 'Hass', the ripe fruit color is a dark purple or black, as classified in the fruit color chart of The New Zealand Institute for Plant & Food Research Ltd.

Figure 6:
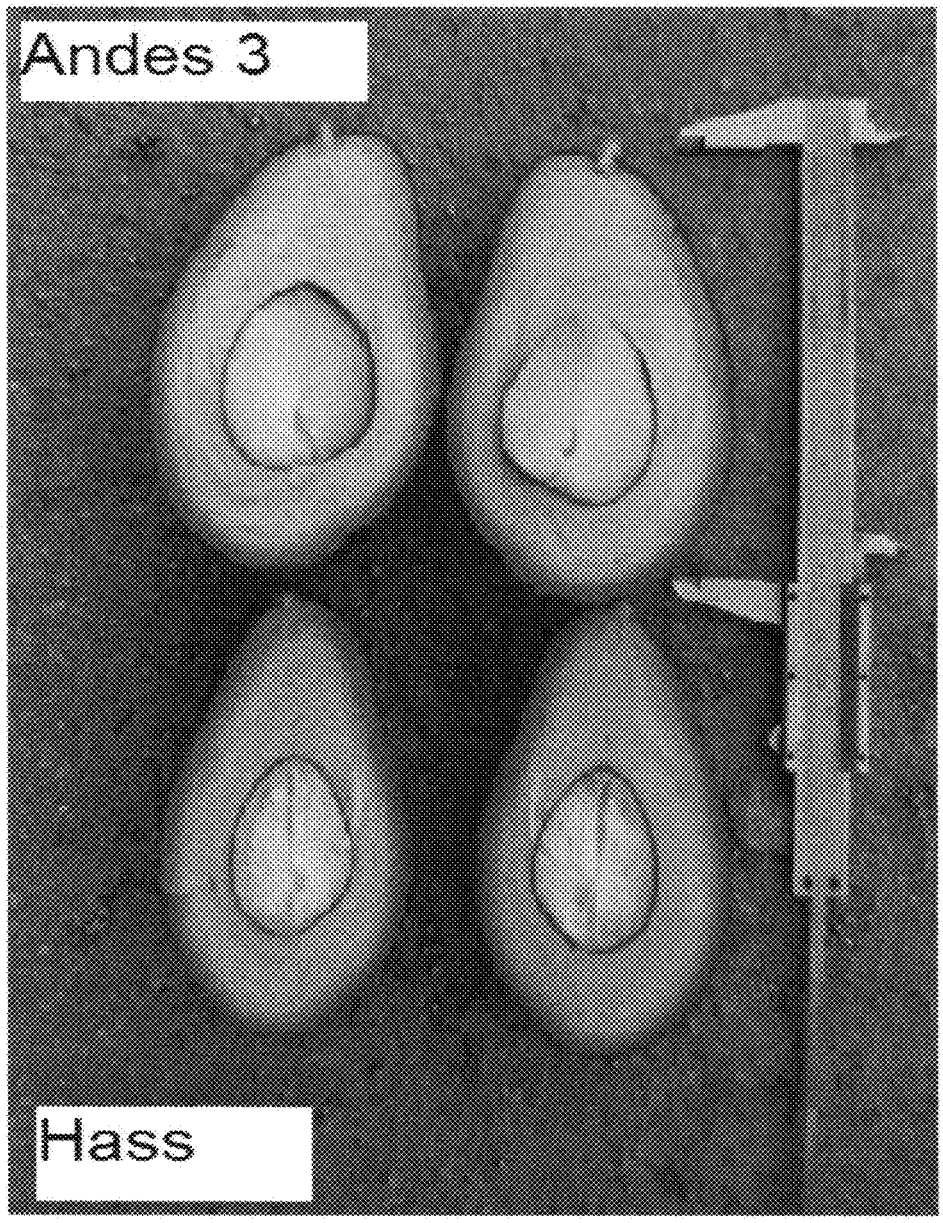
FIG. 6 is a photograph depicting sectioned fruit of the 'Flavia' above regular 'Hass' fruit.

However, unlike 'Hass', the shape in the longitudinal section or lateral view of the seed is generally ovate, as illustrated in FIG. 6. With respect to the fruit shape, the polar/equatorial relation of the fruit is higher in 'Flavia' than in 'Hass', as seen in FIGS. 5 and 6, making the fruit more elongated than 'Hass'. The seed of the 'Flavia' fruit is bigger than that of 'Hass', as shown in FIG. 6, and the seed/pulp relation is greater in 'Flavia' than in 'Hass'. As can be seen in FIG. 5, the fruit of 'Flavia' is much larger than that of regular 'Hass'.

Figure 7:
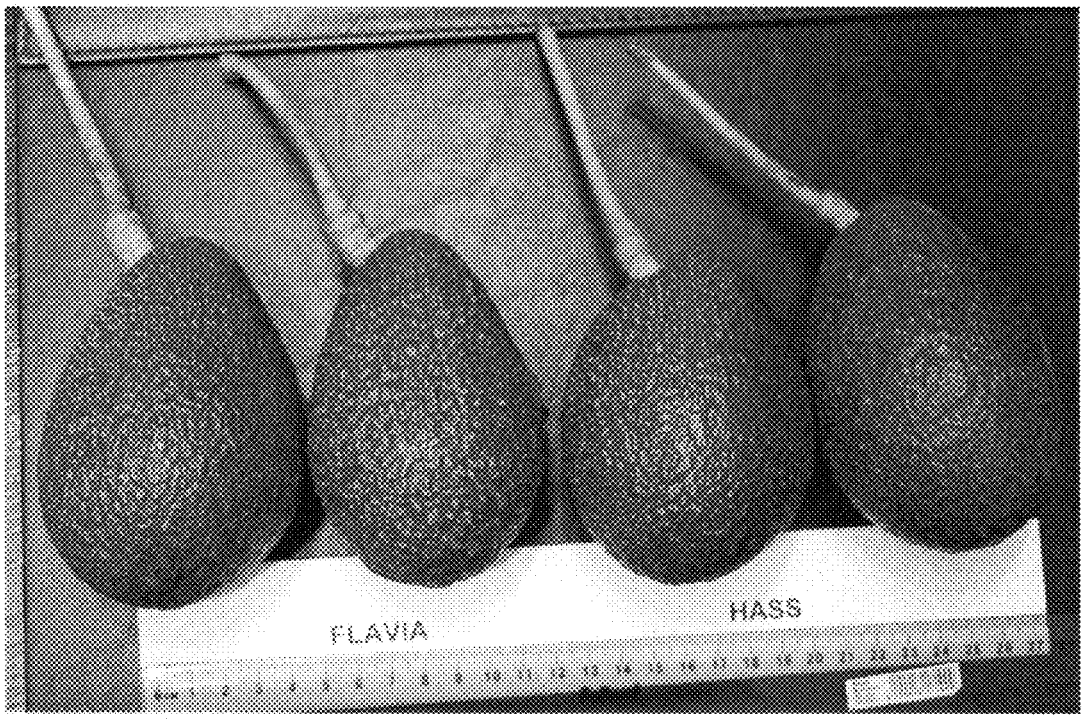
FIG. 7 is a photograph depicting the stem width comparison between 'Flavia' (left) and 'Hass' (right) for similar fruit sizes.
Figure 8:
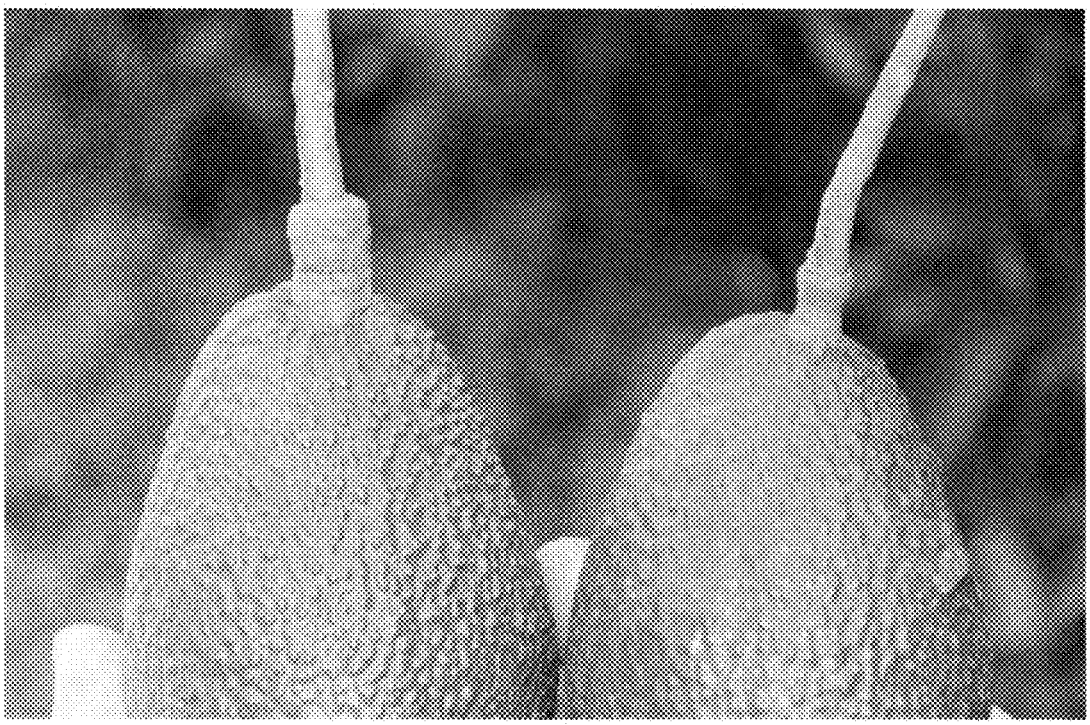
FIG. 8 is a photograph depicting a stem width comparison between 'Flavia' (left) and 'Hass' (right) for similar fruit sizes.

With respect to the fruit, the stem width of the 'Flavia' is greater (11.57 mm) on average than 'Hass' (9.24 mm), as shown in FIGS. 7 and 8.

The following are additional fruit characteristics of 'Flavia':

| | 'Hass' | 'Flavia' |
|---|---|---|
| Stem Color | Pantone 7495C | Pantone 7495C |
| Color of Fruit on Tree (Green) | Pantone 2427C | Pantone 2278C |
| Lenticel Color | Pantone 2294C | Pantone 2293C |

Color of fruit when ripe (according to New Zealand Plant and Food Institute): Purple to Black.

TABLE 2

| Fruit Production per Tree (Kg/Tree) | | |
|---|---|---|
| Year | 'Hass' | 'Flavia' |
| 2003 | 5.8 | 7.1 |
| 2004 | 13.4 | 20.7 |
| 2005 | 30.1 | 30.8 |
| 2006 | 31.7 | 41.0 |

In each row "s" indicates statistical difference (T-Student. P<0.05).

TABLE 3

| Mean Number of fruits per Tree | | |
|---|---|---|
| Year | 'Hass' | 'Flavia' |
| 2003 | 23 | 24 |
| 2004 | 57 | 71 |
| 2005 | 129 | 108 |
| 2006 | 131 | 142.4 |

TABLE 4

| Average fruit Weight (g) | | |
|---|---|---|
| Year | 'Hass' | 'Flavia' |
| 2003 | 248.3 s | 302.7 s |
| 2004 | 236.2 s | 291.1 s |
| 2005 | 234.0 s | 285.3 s |
| 2006 | 242.8 s | 287.9 s |

In each row "s" indicates statistical difference (T-Student. P<0.05).

TABLE 6

| Fruit length (DP). fruit equatorial diameter (DE) and their relation (DP/DE) for each cultivar's fruit | | | |
|---|---|---|---|
| Variety | Polar Diameter (DP). mm | Equatorial diameter (DE). mm | relationship DP/DE |
| 'Hass' | 97.7 s | 70.7 s | 1.38 s |
| 'Flavia' | 106.0 s | 72.6 s | 1.46 s |

In each column "s" indicates statistical difference (T-Student. P<0.05).

TABLE 7

| Results of fruit Characteristics on size 50 fruits | | |
|---|---|---|
| Parameter | 'Hass' | 'Flavia' |
| Seed weight (g) | 24.8 b | 32.2 a |
| Pulp weight (g) | 214.1 b | 207.4 a |
| % seed weight /fruit weight | 10.4 b | 13.4 a |
| Peduncle Insertion * | 1.7 a | 1.9 a |

p < 0.05 Test de Student;
* Stem Insertion Angle: 1 = 70°-90. 2 = 50°-70. 3 = <50°.

p<0.05 Test de Student; * Stem Insertion Angle: 1=70°-90. 2=50°-70°. 3=<50°.

Another distinctive feature of 'Flavia' is that the fruit matures for harvesting four to five weeks earlier than regular 'Hass'. The time of fruit maturity for harvesting, when the fruit reaches minimum dry matter level (23% DM) is medium to late, between 'Fuerte' and 'Hass'.

TABLE 8

| Dates in which cultivar reached harvest maturity(23% Dry Matter) | | |
|---|---|---|
| Year | 'Hass' | 'Flavia' |
| 2003 | 21 August | 24 July |
| 2004 | 09 September | 12 August |
| 2005 | 29 September | 25 August |
| 2006 | 07 September | 03 August |

What is claimed is:

1. A new and distinct variety of avocado tree, substantially as illustrated and described herein.

* * * * *